United States Patent [19]
Klein

[11] Patent Number: 5,817,050
[45] Date of Patent: Oct. 6, 1998

[54] LIPOSUCTION CANNULA

[76] Inventor: Jeffrey A. Klein, 30280 Rancho Viejo Rd., San Juan Capistrano, Calif. 92675

[21] Appl. No.: 865,481

[22] Filed: May 29, 1997

[51] Int. Cl.$^6$ ..................................................... A61M 1/00
[52] U.S. Cl. ............................... 604/35; 604/902; 604/49
[58] Field of Search ................................. 604/35, 22, 19, 604/27, 28, 902, 43, 239, 280, 49

[56] References Cited

U.S. PATENT DOCUMENTS

| | | | |
|---|---|---|---|
| 4,487,600 | 12/1984 | Brownlie et al. | 604/35 |
| 5,186,714 | 2/1993 | Boudreault et al. | 604/35 X |
| 5,203,769 | 4/1993 | Clement et al. | 604/35 X |
| 5,242,386 | 9/1993 | Holzer | 604/22 |
| 5,446,070 | 8/1995 | Mantelle | 514/772.6 |
| 5,453,088 | 9/1995 | Boudewijn et al. | 604/43 |
| 5,472,416 | 12/1995 | Blugerman et al. | 604/35 X |
| 5,514,086 | 5/1996 | Parisi et al. | 604/22 |

OTHER PUBLICATIONS

Jeffrey A. Klein, M.D.; "The Tumescent Technique for Lipo–Suction Surgery", The American Journal of Cosmetic Surgery; vol. 4, No. 4, 1987.

Jeffrey A. Klein, M.D.; "Tumescent Technique for Regional Anesthesia Permits Lidocaine Doses of 35 mg/kg for Liposuction"; J. Dermatol. Surg. Oncol 16:3; Mar. 1990.

Jeffrey Alan Klein, MD*; The Tumescent Technique Anesthesia and Modified Liposuction Technique Dermatologic Clinic; vol. 8, No. 3, Jul. 1990.

Jeffrey A. Klein, M.D.; "Tumescent Technique for Local Anesthesia Improves Safety in Large–Volume Lipsuction"; The American Society of Plastic and Reconstructive Surgeons; Nov. 1993.

Jeffrey A. Klein, M.D.: "Tumescent Technique Chronicals; Local Anesthesia, Liposuction, and Beyond"; Elsevier Science Inc., May. 1995.

Primary Examiner—John D. Yasko
Attorney, Agent, or Firm—Stetina Brunda Garred & Brucker

[57] ABSTRACT

A liposuction cannula constructed of a cannular tube having a proximal open end attachable to a vacuum source and a plurality of apertures disposed laterally through at least one longitudinal segment of the tube. The apertures preferably are situated substantially uniformly about the tube and have a cross-sectional area of about $7.6 \times 10^{-4}$ to about $3.0 \times 10^{-3}$ inch. Inside diameter of the tube is preferably from about 1.2 mm to about 2.2 mm to thereby provide a cannula whose size causes a relatively minimal invasive action through individual incisions through skin to sites of lipid-containing tissue. A method of performing liposuction includes tumescent delivery of a local anesthetic and vasoconstrictor medication to an adipose tissue site and thereafter providing the cannula defined above to the site. The vacuum source is activated and the cannula is moved longitudinally forward and backward within the tissue site. By so doing, the apertures additionally function as a rasp by such longitudinal movement to facilitate disassociation of the lipid from the surrounding tissue.

33 Claims, 1 Drawing Sheet

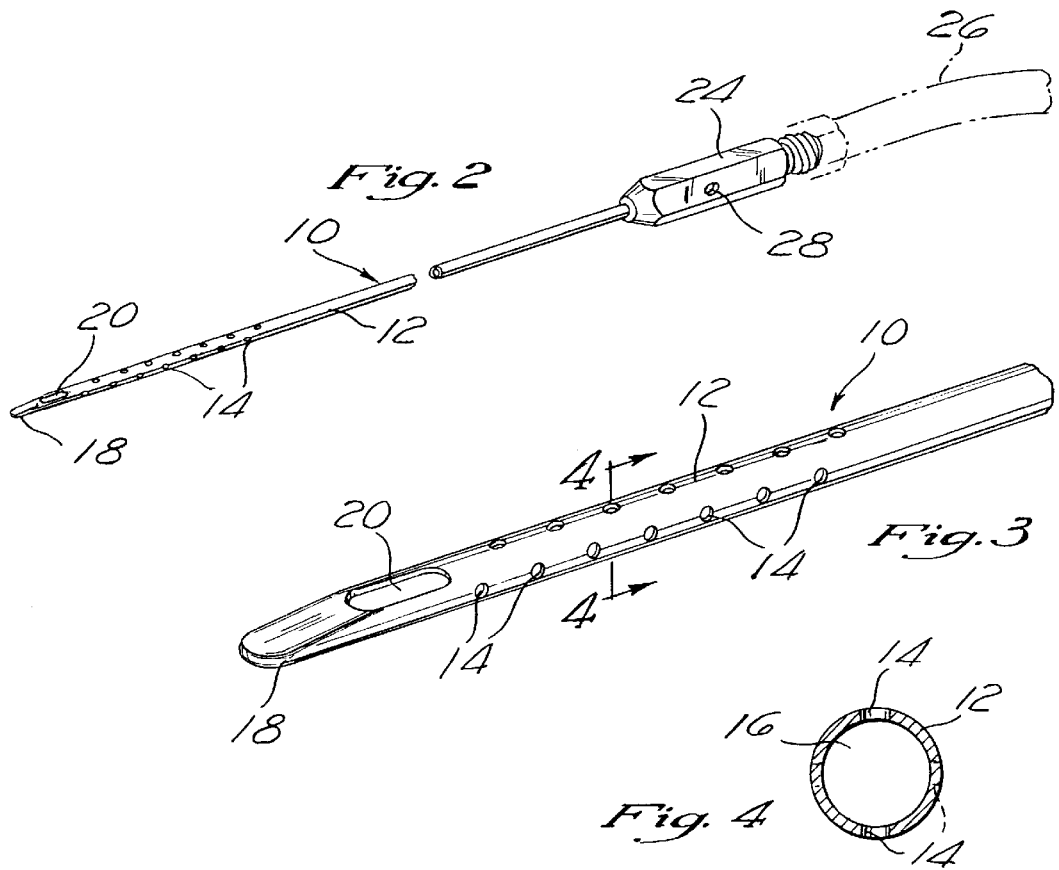

LIPOSUCTION CANNULA

FIELD OF THE INVENTION

This invention relates in general to liposuction devices, and in particular to a liposuction cannula and use thereof wherein the cannula has a plurality of apertures disposed through at least one longitudinal segment of its wall for both blunt rasping action and receiving lipid substrate.

BACKGROUND OF THE INVENTION

Employment of liposuction procedures to remove unwanted fat has developed over the past approximately 20 years. Initially, general anesthesia was an absolute requirement in order to introduce large cannulas into the affected tissue. Typical cannulas were blunt-tipped, and had diameters of 6–10 mm and cross-sectional areas 9–25 times greater than cannulas available today. Common adverse effects included excessive bleeding, prolonged recovery time, and skin disfigurement.

While the above-described devices and technique are still used by some physicians, many dermatologic surgeons now employ a new method broadly known as a tumescent technique which eliminates the requirement of general anesthesia. The term "tumescent technique" means delivering a relatively large volume of a very dilute solution of a local anesthetic agent and a vasoconstrictor agent to the site of liposuction. Thus, the fat removal site is both anesthetized and vasoconstricted so that minimal pain and minimal bleeding occur during the procedure. Concurrently, a small open-tip cannula, generally having a diameter of up to about 2 mm to 3 mm and referred to as a "cannula," is employed for travel through a small incision and positioning at the site of fat removal. Typically, the prior cannula has an open proximal end attachable to a vacuum source to thereby draw lipid substrate through one to three openings at the tip of the cannula and thereafter proximally to the vacuum source.

While the above-described cannula is effective in performing liposuction surgery, it has only one to three tip-disposed openings through which adipocytes and lipid substrate can enter for subsequent travel through the cannula to an external collection site in association with the vacuum source. Additionally, certain site specific adipose tissue, such as that associated with breast tissue, for example, exhibits a greater cohesiveness with adjacent fibrous tissue structure and is therefore more difficult to remove because the surface of the prior art cannula is smooth, and does not provide gentle blunt rasping qualities that can enhance lipid substrate disassociation.

In view of the above-described prior cannula construction, it is apparent that a need is present for a cannula having greater capabilities both in volume removal of adipose tissue and in rasping ability for facilitating disassociation of adipocytes from surrounding fibrous tissue. Accordingly, a primary object of the present invention is to provide a new cannula where at least one longitudinal segment of its wall has disposed therethrough a plurality of apertures through which adipocytes and lipid substrate can pass.

Another object of the present invention is to provide a cannula wherein the plurality of apertures are disposed substantially uniformly and provide a rasping function when moved within tissue.

Yet another object of the present invention is to provide a method of performing liposuction employing a tumescent technique and using a cannula with a plurality of apertures disposed substantially uniformly about at least one longitudinal distal segment of its wall.

These and other objects of the present invention will become apparent throughout the description of the invention which now follows.

SUMMARY OF THE INVENTION

The present invention is a liposuction cannula comprising a cannular tube having a proximal open end attachable to a vacuum source and a plurality of apertures disposed laterally through at least one longitudinal distal segment of the tube. The apertures preferably are situated substantially uniformly and have a cross-sectional area of about $7.6 \times 10^{-4}$ to about $3.0 \times 10^{-3}$ inch. Inside diameter of the tube is preferably from about 1.2 mm to about 2.2 mm to thereby provide a cannula whose size causes a relatively minimal invasive traumatic action through smaller individual incisions through skin to sites of adipose tissue.

The present invention includes a method of performing liposuction at a lipid-containing tissue site through incorporation of the above-described cannula with a tumescent technique as earlier defined. The method comprises, first, providing to the tissue site a tumescent quantity of a solution comprising a clinically effective dosage of a local anesthetic and a vasoconstrictor, followed by introduction of a liposuction cannula, as defined above, within the tissue site. The proximal open end of the cannula is attached to a vacuum source and the vacuum source is activated while longitudinally moving the cannula forward and backward within the subcutaneous adipose tissue. Adipocyte entrance from the adipose tissue site into the cannula through the apertures is thereby effectuated, and the multiple blunt, non-cutting apertures essentially function as a gentle rasp ripping rather than cutting with such longitudinal movement of the cannula to thereby promote disassociation of the adipocytes from the surrounding tissue. Specific employment of this method in lipid-containing breast tissue accomplishes breast size reduction through the removal or destruction of adipocytes.

The small cross-sectional size of the present cannula allows it to easily transverse highly fibrous adipose tissue such as that found in the female breast. While the additive effect of multiple small apertures produces a highly efficient aspiration of fat, each individual aperture is so small that surgical trauma to sensory nerves, blood vessels and lymphatic vessels is minimized. When comparing cannulas having similar designs, their efficacy can be quantified by measuring the volume of fat a specific cannula can aspirate with any given number of strokes through comparable fatty tissue. In this type of comparison, if a first cannula removes more fat than a second cannula, then the first cannula is more efficient. It is recognized that for cannulas of similar design, the greater the inside diameter or the greater the cross sectional area of the lateral openings, the greater the efficiency. In this regard, a cannula of the present invention with a 1.8 mm inside diameter has an efficiency at least as good as a prior art cannula with a 2.2 mm inside diameter. In addition to greater efficiency, the small cross sectional dimension of the present cannula accomplishes smaller incisions, less-apparent scars, more incisions, increased smoothness of results, more aggressive liposuction with less pain under local anesthesia, and multiple entry portals to more widely distribute the process of detaching fat tissue.

BRIEF DESCRIPTION OF THE DRAWINGS

An illustrative and presently preferred embodiment of the invention is shown in the accompanying drawings in which:

FIG. 1 is a perspective view of a cannula inserted within tissue containing lipid substrate;

FIG. 2 is a perspective view of the cannula of FIG. 1 attached to a vacuum source;

FIG. 3 is an enlarged perspective view of a portion of the cannula of FIGS. 1 and 2; and FIG. 4 is a cross section view along line 4—4 of FIG. 3.

DETAILED DESCRIPTION OF THE PREFERRED EMBODIMENT

FIGS. 1 and 2 demonstrate a cannula 10 and the use thereof within adipose tissue 22. In particular, the cannula 10 is attached to a handle 24 which is attached to tubing 26 functioning as a vacuum source attached at its other end to a vacuum pump (not shown). The handle 24 has a conventional thumb-controlled hole 28 such that vacuum is maintained when a user's thumb 30 covers the hole 28 and disappears when the thumb 30 is lifted. The cannula 10 is introduced into tissue 22 as described later to thereby remove lipid substrate.

FIGS. 3 and 4 show in greater detail the construction of the cannula 10. In particular, the cannula 10 comprises a cannular tube 12 having a proximal open end (not shown) attachable to the vacuum source tubing 26 through the handle 24 within which the open end is situated in FIGS. 1 and 2. A plurality of uniformly situated, generally circular apertures 14 are disposed laterally through at least one longitudinal segment of the tube 12, and have a diameter of about $\frac{1}{32}$ inch to about $\frac{1}{16}$ inch. The cross sectional area of each of these apertures 14 is therefore about $7.6 \times 10^{-4}$ inch to about $3.0 \times 10^{-3}$. Such uniform distribution of the apertures 14 maximize structural rigidity and integrity of the cannula 10 while concurrently providing beneficial openings. In the non-limiting embodiment illustrated, four rows of seven apertures are in off-set arrangement longitudinally along the tube 12 over a segment length of about 1.0 to 1.5 inch, with each row in one respective quadrant of the tube 12. Hard-tempered stainless steel hypodermic needle stock is used in cannula construction, and an inside diameter of the tube 12 is preferably from about 1.2 mm to about 2.2 mm. The distal end 18 of the tube 12 has one conventional opposing in-line, oblong openings 20, visible in FIGS. 2 and 3.

Methodology for removing lipid substrate from tissue includes first conventionally providing to the tissue site a tumescent quantity of a solution comprising a clinically effective dosage of a topical anesthetic and a vasoconstrictor. Thereafter, the proximal open end of the cannula 10 is attached to the vacuum source tubing 26 through the handle 24. The cannula 10 then is placed within adipose tissue 22 as known in the art through a small incision 32 leading through the skin to the site of adipose tissue. Once the cannula 10 is in place, the vacuum source is activated and the surgeon grasps the handle 24 as shown in FIG. 1 and controls vacuum delivery through thumb coverage of the thumb hole 28 described above while moving the cannula forward and backward within the tissue 22 at the site of adipose tissue. Such movement provides a rasping force by the apertures 14 on the adipose tissue and thereby facilitates adipocyte disassociation from surrounding fibrous tissue. Adipose tissue so presented enters the interior 16 of the tube 12 through the apertures 14 for final removal. Multiple sites are treated through multiple small incisions as would be recognized in the art.

Fat removal according to the present invention includes female breast size reduction which can be accomplished through this methodology whereby adipose tissue is aspirated by the apertures 14 during repeated reciprocal movement of the cannula 10 within a plurality of tissue sites reachable through respective small incisions as earlier described. In this manner, adipose tissue removal from the female breast is highly effective, and obviates the large surgical excision of breast skin and adipose tissue with its associated pain, scarring and prolonged recovery time. Tumescent liposuction of the female breast using the canula of the present invention is performed totally under local anesthesia, thereby eliminating the need for general anesthesia.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A liposuction cannula comprising a cannular tube having a proximal open end attachable to a vacuum source, an inside diameter not exceeding about 2.2 mm, and at least five apertures disposed laterally through at least one longitudinal segment of the tube, with the cross-sectional area of each aperture from about $7.6 \times 10^{-4}$ to about $3.0 \times 10^{-3}$ inch.

2. A liposuction cannula as claimed in claim 1 wherein the tube has an inside diameter from about 1.2 mm to about 2.2 mm.

3. A liposuction cannula as claimed in claim 2 wherein the apertures are situated substantially uniformly.

4. A liposuction cannula as claimed in claim 3 wherein the cross-sectional area of each aperture is from about $7.6 \times 10^{-4}$ to about $3.0 \times 10^{-3}$ inch.

5. A liposuction cannula as claimed in claim 4 wherein each of the apertures is substantially circular.

6. A liposuction cannula as claimed in claim 5 wherein each of the apertures has a diameter of about $\frac{1}{32}$ inch to $\frac{1}{16}$ inch.

7. A liposuction cannula as claimed in claim 1 wherein the apertures are situated substantially uniformly.

8. A liposuction cannula as claimed in claim 2 wherein the cross-sectional area of each aperture is from about $7.6 \times 10^{-4}$ to about $3.0 \times 10^{-3}$ inch.

9. A liposuction cannula as claimed in claim 1 wherein the cross-sectional area of each aperture is from about $7.6 \times 10^{-4}$ to about $3.0 \times 10^{-3}$ inch.

10. A liposuction cannula as claimed in claim 9 wherein each of the apertures is substantially circular.

11. A liposuction cannula comprising a cannular tube having a proximal open end attachable to a vacuum source, an inside diameter from about 1.2 mm to about 2.2 mm, and at least five apertures disposed laterally through at least one longitudinal segment of the tube, with the cross-sectional area of each aperture from about $7.6 \times 10^{-4}$ to about $3.0 \times 10^{-3}$ inch.

12. A method of performing liposuction at an adipose tissue site, the method comprising:
   a) providing to the tissue site a tumescent quantity of a solution comprising a clinically effective dosage of a local anesthetic and a vasoconstrictor;
   b) providing a liposuction cannula comprising a cannular tube having a proximal open end attachable to a vacuum source, an inside diameter not exceeding about 2.2 mm, and at least five apertures disposed laterally through at least one longitudinal segment of the tube, with the cross-sectional area of each aperture from about $7.6 \times 10^{-4}$ to about $3.0 \times 10^{-3}$ inch;

c) placing the liposuction cannula within the adipose tissue site and attaching its proximal open end to a vacuum source; and d) activating the vacuum source while longitudinally moving the cannula forward and backward within the tissue site, thereby effectuating adipocyte entrance from the adipose tissue site into the cannula through the apertures.

13. A method as claimed in claim 12 wherein the tube has an inside diameter from about 1.2 mm to about 2.2 mm.

14. A method as claimed in claim 13 wherein the apertures of the tube are situated substantially uniformly.

15. A method as claimed in claim 14 wherein the cross-sectional area of each of the apertures of the tube is from about $7.6 \times 10^{-4}$ to about $3.0 \times 10^{-3}$ inch.

16. A method as claimed in claim 15 wherein each of the apertures is substantially circular.

17. A method as claimed in claim 16 wherein each of the apertures of the tube has a diameter of about 1/32 inch to 1/16 inch.

18. A method as claimed in claim 12 wherein the apertures are situated substantially uniformly.

19. A method as claimed in claim 13 wherein the cross-sectional area of each aperture is from about $7.6 \times 10^{-4}$ to about $3.0 \times 10^{-3}$ inch.

20. A method as claimed in claim 12 wherein the cross-sectional area of each aperture is from about $7.6 \times 10^{-4}$ to about $3.0 \times 10^{-3}$ inch.

21. A method as claimed in claim 20 wherein each of the apertures is substantially circular.

22. A method as claimed in claim 21 wherein each of the apertures of the tube has a diameter of about 1/32 inch to 1/16 inch.

23. A method of performing liposuction at an adipose-containing breast tissue site, the method comprising:

a) providing to the breast tissue site a tumescent quantity of a solution comprising a clinically effective dosage of a local anesthetic and a vasoconstrictor;

b) providing a liposuction cannula comprising a cannular tube having a proximal open end attachable to a vacuum source, an inside diameter not exceeding about 2.2 mm, and at least five apertures disposed laterally through at least one longitudinal segment of the tube, with the cross-sectional area of each aperture from about $7.6 \times 10^{-4}$ to about $3.0 \times 10^{-3}$ inch;

c) placing the liposuction cannula within the breast tissue site and attaching its proximal open end to a vacuum source; and d) activating the vacuum source while longitudinally moving the cannula forward and backward within the breast tissue site, thereby effectuating adipocyte entrance from the breast tissue site into the cannula through the apertures.

24. A method as claimed in claim 23 wherein the tube has an inside diameter from about 1.2 mm to about 2.2 mm.

25. A method as claimed in claim 24 wherein the apertures of the tube are situated substantially uniformly.

26. A method as claimed in claim 25 wherein the cross-sectional area of each of the apertures of the tube is from about $7.6 \times 10^{-4}$ to about $3.0 \times 10^{-3}$ inch.

27. A method as claimed in claim 26 wherein each of the apertures is substantially circular.

28. A method as claimed in claim 27 wherein each of the apertures of the tube has a diameter of about 1/32 inch to 1/16 inch.

29. A method as claimed in claim 23 wherein the apertures are situated substantially uniformly.

30. A method as claimed in claim 23 wherein the cross-sectional area of each aperture is from about $7.6 \times 10^{-4}$ to about $3.0 \times 10^{-4}$ inch.

31. A method as claimed in claim 23 wherein the cross-sectional area of each aperture is from about $7.6 \times 10^{-4}$ to about $3.0 \times 10^{-3}$ inch.

32. A method as claimed in claim 31 wherein each of the apertures is substantially circular.

33. A method as claimed in claim 32 wherein each of the apertures of the tube has a diameter of about 1/32 inch to 1/16 inch.

\* \* \* \* \*